(12) United States Patent  (10) Patent No.: US 8,315,695 B2
Sebelius et al.  (45) Date of Patent: Nov. 20, 2012

(54) SYSTEM AND METHOD FOR WIRELESS GENERATION OF STANDARD ECG LEADS AND AN ECG SENSING UNIT THEREFOR

(75) Inventors: Fredrik Sebelius, Lund (SE); Jonas Tilly, Lomma (SE)

(73) Assignee: Novosense AB, Lund (SE)

( * ) Notice: Subject to any disclaimer, the term of this patent is extended or adjusted under 35 U.S.C. 154(b) by 1037 days.

(21) Appl. No.: 12/279,614

(22) PCT Filed: Feb. 2, 2007

(86) PCT No.: PCT/SE2007/050059
§ 371 (c)(1),
(2), (4) Date: Aug. 15, 2008

(87) PCT Pub. No.: WO2007/094729
PCT Pub. Date: Aug. 23, 2007

(65) Prior Publication Data
US 2010/0234746 A1   Sep. 16, 2010

(30) Foreign Application Priority Data
Feb. 15, 2006 (SE) ........................ 0600328

(51) Int. Cl.
*A61B 5/0402* (2006.01)
(52) U.S. Cl. ........................................ 600/509
(58) Field of Classification Search .................. 600/509
See application file for complete search history.

(56) References Cited

U.S. PATENT DOCUMENTS

| 3,943,918 A | 3/1976 | Lewis |
| 4,243,044 A | 1/1981 | Blancke |
| 4,850,370 A | 7/1989 | Dower |
| 4,981,874 A | 1/1991 | Latter et al. |
| 5,058,598 A | 10/1991 | Nicklas et al. |
| 5,168,874 A | 12/1992 | Segalowitz |
| 5,307,818 A | 5/1994 | Segalowitz |
| 5,427,111 A | 6/1995 | Traub et al. |
| 5,862,803 A | 1/1999 | Besson et al. |

(Continued)

OTHER PUBLICATIONS

Scherer et al., "Synthesis of the 12 Lead Electrocardiogram from a 3 Lead Semi.-Orthogonal Subset Using Patient-Specific Linear Transformation Arrays", Computers in Cardiology, 1988. Proceedings. Washington, DC, USA Sep. 25-28, 1988, Washington, DC, USA, IEE Comput. Soc. Pr, US (ISBN 0-8186-1949-X) p. 449-451 (1988).

(Continued)

*Primary Examiner* — Eric D. Bertram
(74) *Attorney, Agent, or Firm* — Volpe and Koenig, P.C.

(57) ABSTRACT

A system for wireless generation of at least one standard ECG lead comprises a plurality of electrodes for application to a subject at separate points thereof and a remote receiver station for generating at least one standard ECG lead from signals detected by a first group of said plurality of electrodes. The system further comprises a wireless sensing unit for generating at least two non-standard ECG signals from bipolar signals detected by a second group of the plurality of electrodes, a processor in the remote receiver station for calculation of a transform synthesizing each generated standard ECG lead from at least two of the non-standard ECG signals, a disconnection unit for disconnection of the first group of electrodes from the subject following the calculation, and a transfer unit for wireless transferring of the non-standard ECG signals to the remote receiver station following the disconnection of the first group of electrodes.

13 Claims, 9 Drawing Sheets

U.S. PATENT DOCUMENTS

| | | |
|---|---|---|
| 5,957,854 A | 9/1999 | Besson et al. |
| 6,026,321 A | 2/2000 | Miyata et al. |
| 6,132,371 A | 10/2000 | Dempsey et al. |
| 6,289,238 B1 | 9/2001 | Besson et al. |
| 6,416,471 B1 | 7/2002 | Kumar et al. |
| 6,441,747 B1 | 8/2002 | Khair et al. |
| 6,453,186 B1 | 9/2002 | Lovejoy et al. |
| 6,494,829 B1 | 12/2002 | New, Jr. et al. |
| 6,496,705 B1 | 12/2002 | Ng et al. |
| 6,526,310 B1 | 2/2003 | Carter et al. |
| 6,551,252 B2 | 4/2003 | Sackner et al. |
| 6,567,680 B2 | 5/2003 | Swetlik et al. |
| 6,577,893 B1 | 6/2003 | Besson et al. |
| 6,579,242 B2 | 6/2003 | Bui et al. |
| 6,589,170 B1 | 7/2003 | Flach et al. |
| 6,611,705 B2 | 8/2003 | Hopman et al. |
| 6,804,550 B1 | 10/2004 | Murray |
| 6,901,285 B2 | 5/2005 | Schreck |
| 7,974,684 B2 * | 7/2011 | Stewart .................. 600/509 |
| 2002/0045836 A1 | 4/2002 | Alkawwas |
| 2005/0043640 A1 | 2/2005 | Chang |

OTHER PUBLICATIONS

Ljupco Hadzievski et al., "A Novel Mobile Transtelephonic System With Synthesized 12-Lead ECG", IEEE Transactions on Information Technology in Biomedicine (ISSN 1089-7771) vol. 8 (4) p. 428-438 (2004).

Rubel F.P. et al., "Toward Personal eHealth in Cardiology. Results from the EPI-MEDICS Telemedicine Project". Journal of Electrocardiology (ISSN 0022-0736) vol. 38 (4), p. 100-106 (2005).

* cited by examiner

SYSTEM AND METHOD FOR WIRELESS GENERATION OF STANDARD ECG LEADS AND AN ECG SENSING UNIT THEREFOR

TECHNICAL FIELD

The present invention generally relates to cardiac monitoring of a human or animal subject. More particularly, the present invention pertains to a system for wireless generation of standard ECG leads and to a method for wireless generation of such standard ECG leads. The invention further relates to an ECG unit for use in said system.

BACKGROUND OF THE INVENTION

The cardiac cycle can be described as the activation of certain specialized heart conduction cells in a predictable sequence, which leads to a coordinated and sequential contraction of the arterial and ventricular muscle fibers. The electrical signal associated with the muscle action is transmitted through various tissues and ultimately reaches the surface of the body, where it can be measured. Such a measurement is called ECG which stands for electrocardiogram.

Electrical equipment for such measurements is used for monitoring and/or recording ECG data and may be stationary or portable.

The stationary ECG equipments are electrical monitoring and recording devices which are connected to a patient by wires. In current use, such monitors utilize surface electrodes located on the body of the patient and connected by wires to an electrocardiograph machine, which allows the detected heart signals to be displayed on a paper strip or a monitor. However, the use of such wiring limits the mobility of the patient and requires the patient to remain in bed throughout the monitoring.

The portable ECG equipments can be divided into recorders and transmitters. In both cases wires from multiple electrodes applied to the body of a patient are connected to a recorder or transmitter unit, hung around the patient's neck. These units are often burdensome. The recorder unit is a self-contained unit such that the patient may move around. The transmitter unit further contains some sort of radio equipment, which makes it possible for the patient to move around and still be monitored by a stationary unit receiving the measuring data signals from the transmitter unit.

A common problem with electrodes and wires is the risk of detachment from the patient, as the wires and electrodes may be exposed to high tensile forces, the total required length of wires often being in the range of one meter.

Moreover, the measurements and displayed curves may be influenced by physical pressure or strains on the electrodes.

Thus, the problem with wires or electrodes that are pulled off remains with all the described equipments.

Prior art systems of the above described types are disclosed in inter alia U.S. Pat. Nos. 4,243,044; 5,427,111; 6,026,321; 6,416,471; 6,453,186; 6,494,829; 6,526,310; 6,551,252; 6,567,680; 6,579,242; 6,589,170 and 6,611,705.

Methods of acquiring ECG have been proposed to exclude all wires and integrate the ECG recording and radio transmitter in every sensing unit, e.g. disclosed in U.S. Pat. Nos. 3,943,918; 4,981,874; 5,168,874; 5,307,818; 5,862,803; 5,957,854; 6,289,238; 6,132,371; 6,441,747; 6,496,705 and 6,577,893.

In U.S. Pat. Nos. 4,850,370; 5,058,598 and 6,901,285, the basic idea is based on first transforming a reduced number of the ECG measurements to one equivalent X, Y, Z source and then deriving the standard leads by using the equivalent voltage source and the "known" impedance of the body. The major problem with this approach is that the impedance variation between people is large. Therefore, the ECG estimate will sometimes be totally wrong, if the impedance is not measured. Thus, the ECG signal measured with these proposed solutions is incorrect and can not be used in for diagnosis. These systems have therefore never come to clinical use.

U.S. Patent Appl. Publ. No. 2002/0045836 A1 discloses a surveillance system for wireless transfer of signals from a number of electrodes positioned on a subject and each having its own contacts to a base station being capable of controlling the electrodes in several respects. More precisely, four electrodes positioned in the corners of an elongate rectangle the long sides of which are parallel to the direction of the standard lead and the short sides of which are positioned substantially in where the standard leads are detected and orthogonal to the long sides. The electrode contacts of each short side are elements of a separate electrode.

In U.S. Patent Appl. Publ. No. 2002/0045836 A1 the body is assumed to act solely resistively and homogenously which is a major simplification leading to the use of a predetermined scalar factor that will give a false and clinically useless standard lead.

DISCLOSURE OF THE INVENTION

It is a primary object of the present invention to provide a system and a method for wireless generation of at least one correct and clinically useful standard ECG lead which eliminates the problems of using wires, thereby enabling the patient to move freely without any risk related to wires during such movement.

A further object of the invention is to provide a wireless ECG sensing unit which is adapted for use in said system.

The primary object is achieved by a system for wireless generation of at least one standard ECG lead as defined in claim 1 and by a method for wireless generation of at least one standard ECG lead as defined in claim 14.

The further object of the invention is achieved by a wireless ECG sensing unit as defined in claim 11.

Preferred embodiments of the inventive system, method and sensing unit are defined in the dependent claims.

Thus, a system for wireless generation of at least one standard ECG lead comprises a plurality of electrodes for application to a subject at separate points thereof and a remote receiver station having means for generating at least one standard ECG lead from signals detected by a first group of said plurality of electrodes. This system further comprises means for generating at least two non-standard ECG signals from bipolar signals detected by a second group of said plurality of electrodes substantially simultaneously with the signal detection by said first group of said plurality of electrodes, said second group of said plurality of electrodes comprising at least one subset having at least three closely located electrodes arranged non-linearly for detecting two local bipolar signals; processor means in said remote receiver station for calculation of a transform synthesizing each generated standard ECG lead from at least two of said non-standard ECG signals: means for disconnection of said first group of electrodes from said subject following said calculation, said processor means thereafter synthesizing said standard ECG lead from said non-standard ECG signals solely using said transform; and means for wireless transferring of said non-standard ECG signals to said remote receiver station following said disconnection of said first group of electrodes. Thereby said at least one standard ECG lead is wireless generated by said synthesizing following the disconnection of said first group of electrodes.

Thus, this solution makes it possible for the patient, following the calculation of the transform synthesizing each generated standard ECG lead, to move freely without any wires applied to him or her.

As a consequence of the non-linear arrangement, the three electrodes in said subset may be used as two different pairs, where each pair detects a separate bipolar signal having unique components of the electric signal generated during each cardiac contraction.

By arranging the three electrodes along two orthogonal lines, said two bipolar signals will contain orthogonal components of said electric signal generated during each cardiac contraction. This will obviously facilitate the synthesizing of the standard ECG lead.

Preferably, said subset of said second group of electrodes are elements of a wireless ECG sensing unit, such that the relative positions of the electrodes are fixed, and the wireless ECG sensing unit may further comprise a radio module for communication with said remote receiver station when activated thereby.

Preferably, the wireless ECG sensing unit further comprises a differential amplifier for each bipolar signal constituting said means for generating non-standard ECG signals, and a data processor connected between said differential amplifiers and said radio module and adapted for digital storing of the non-standard ECG signals.

Also, the wireless ECG sensing unit may further comprise at least one further differential amplifier having inputs connectable to separate ones of said plurality of electrodes and an output connected to said data processor.

Further, said disconnection unit may comprise wires connected to the electrodes in said first group of said plurality of electrodes and switching means for selecting the electrodes to be connected to said at least one further differential amplifier. In this embodiment, said disconnection unit may also comprise wires each connected to one electrode in a separate wireless ECG sensing unit.

Preferably, each wireless ECG sensing unit comprises means for controlling the switching means, e.g. in accordance with instructions received from said remote receiver station.

In normal operation, the above system comprises at least one further ECG sensing unit, and means in said remote receiver station for synchronizing data flow from the ECG sensing units. Thereby, several standard ECG leads may be generated substantially simultaneously.

The method of wireless generating a standard ECG lead comprises the steps of generating a standard ECG lead using electrodes for application to a subject at standard positions thereof; substantially simultaneously generating at least two non-standard ECG signals from bipolar signals detected by a further group of at least three electrodes for application to a subject at adjacent positions; calculating a transform synthesizing said standard ECG lead from said non-standard ECG signals; interrupting the generation of said standard ECG lead following said calculation; transferring said non-standard ECG signals wireless at least following said interruption; and thereafter generating said standard ECG lead solely using said calculated transform.

Preferably, the generating of the standard ECG lead comprises using wires connected to the corresponding electrodes and said interrupting comprises detaching these electrodes and wires. However, the non-standard ECG signals may be transferred wireless at all times. Also, the standard ECG lead and the non-standard ECG signals are preferably generated substantially simultaneously. Further, the calculation may be based upon digitally stored representations of the standard ECG lead and of the non-standard ECG signals.

The ECG sensing unit comprises at least three electrodes for application to a subject and generating bipolar signals; a radio module for communication with a remote receiver station; a differential amplifier for each bipolar signal for generating a non-standard ECG signal; a data processor connected between said differential amplifiers and said radio module, for digital storing of the non-standard ECG signals; and at least one further differential amplifier having inputs connectable to separate ones of a plurality of further electrodes and an output connected to said data processor.

The ECG sensing unit may further comprise means responsive to external signals for controlling its operation and the electrodes may be part of a patch detachable from the rest of the ECG sensing unit.

BRIEF DESCRIPTION OF THE DRAWINGS

The accompanying drawings illustrate preferred embodiments of a system and an ECG sensing unit according to the present invention, in which.

DESCRIPTION AF THE PREFERRED EMBODIMENTS

Figure 1:
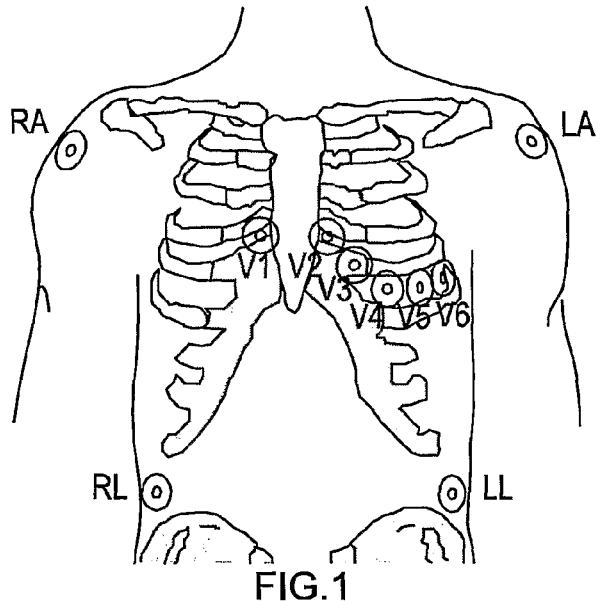
FIG. 1 is a schematic front view of human torso showing the electrode positions used when measuring a standard 12-lead.

Referring to FIG. 1, the electrodes for ECG measurements are localized on different parts of the body.

The normal electrocardiogram or rhythm-monitoring strip is obtained from one of three types of electrical connections. These connections are known as limb leads, augmented limb leads and precordial leads. Here it should be noted that the term "lead" is used herein in the medical sense and not the electrical sense, i.e. a "lead" is not a wire but a linear combination of voltage potentials from two or several anatomical defined position on the body where the heart signal is sensed.

The standard 12-lead electrocardiogram requires ten wires to be attached by electrodes to the body of the patient. All wires are then connected to one electrocardiograph unit in order to detect heart signals and transform them into a 12-lead electrocardiogram. Three of the 12-leads are bipolar recordings while the rest are unipolar recordings. A bipolar recording is a recorded voltage difference between two anatomical defined electrode positions. The bipolar leads are as follows:
lead I is the electrical potential difference between the arms, LA–RA (FIG. 1);
lead II is the electrical potential difference between the left leg and the right arm, LL–RA (FIG. 1);
lead III is the electrical potential difference between the left leg and the left arm. LL–LA (FIG. 1);

However, in practice electrodes could often be placed on the body towards the arms and legs, see FIG. 1, to avoid discomfort for the patient and wires coming loose during long term registration. A unipolar measurement is a measurement from one site on the body where the electrical potential is varying, in relation to a zero varying potential reference. There is however no true zero varying potential references on the body as the ECG propagates throughout the entire body. A zero varying potential reference was therefore created by N. F. Wilson et al. by weighting the electrical potentials from the left arm, left leg and right arm with three 5 kΩ resistors, i.e. 1/3*(RA+LA+LL). This voltage reference is called Wilson central terminal (CT) but is still not an absolute zero varying reference. However, as it has been used for such a long time it has become the standard.

The augmented limb leads are referred to as unipolar leads. Each of them is the difference between the potential at one site and the potentials at two other anatomical defined positions. Thus, the augmented limb leads are linear combinations of the bipolar limb leads. The augmented leads are as follows:
aVR—the "unipolar" right arm lead, i.e. RA–1/2*(LA+LL)
aVL—the "unipolar" left arm lead, i.e. LA–1/2*(RA+LL)
aVF—the "unipolar" left leg lead, i.e. LL–1/2*(RA+LA)

The reference voltage for the augmented leads is created by connecting the right arm, left arm and left leg with two 5 kΩ resistors in three different ways: left arm and left leg, right arm and left leg and finally right arm and left arm (for aVR, aVL and aVF, respectively). These electrical reference potentials are later referred to as CT/aVR, CT/aVL and CT/aVF.

The precordial leads are also unipolar, but unlike the augmented limb leads, one or more precordial electrodes are connected to the chest wall. The reference source is again potentials weighted together and does not vary significantly with the cardiac cycle. Wilson central terminal (CT) is typically used as reference. In standard settings there are six precordial leads V1-V6 where the numeral represents the exact location on the chest.

Thus, this involves attaching six electrodes to the chest or precordial area, and attaching four electrodes on the body towards the arms and legs of the patient; see FIG. 1.

Figure 2A:
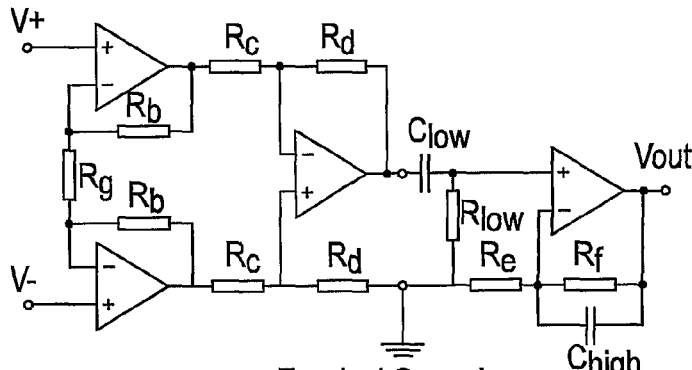
FIG. 2A is a circuit diagram of an ECG amplifier and FIG. 2B is a corresponding block diagram.
Figure 2B:
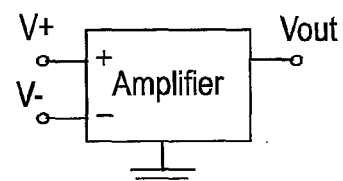
Figure 3:
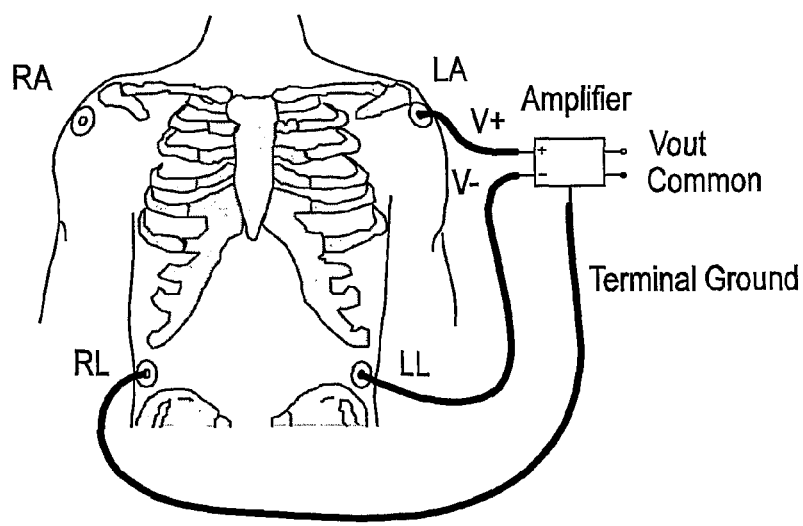
FIG. 3 illustrates a typical electric connection of an ECG amplifier.

Independent of the measurement type, bipolar or unipolar, the same type of amplifier has been used to generate the signals. This amplifier is shown in FIGS. 2A, 2B and 3 and has three connections to the body; two electrode locations where the electrical potential difference is measured and one electrode connection for the patient ground, see FIG. 3. The patient ground connection, normally right leg (RL), has the only purpose of driving the terminal ground of the amplifier to the same level as the patient ground, thereby driving the amplifier within working potential. The ground connection is sometimes actively driven, i.e. a guard, to suppress noise. In an ECG amplifier that has more than one lead, the terminal grounds for all amplifiers are interconnected and only one wire is connected to the patient ground. The connection from terminal ground to patient ground is often performed through an amplifier or a resistor as the current must be kept below a specified threshold. There exist systems that instead of using a separate ground wire drive the two (or more) measuring electrodes to a common terminal ground potential. However, distant measurement references, as RA, LA, LL, are still needed to perform the different ECG measurements. A high common mode rejection ratio (CMRR) is preferable to suppress common node noise, e.g. the 50 or 60 Hz power capacitively linked to the body. To maintain a high CMRR the input impedance must also be high (>10 MΩ) as the connection impedance to the body typically varies in the range of 1-3 kΩ.

Generally, the ECG amplifier contains a band pass filter for the frequencies of interest, which by standard should be 0.05-100 Hz. This could however vary quite a lot depending on manufacturer.

Figure 4:
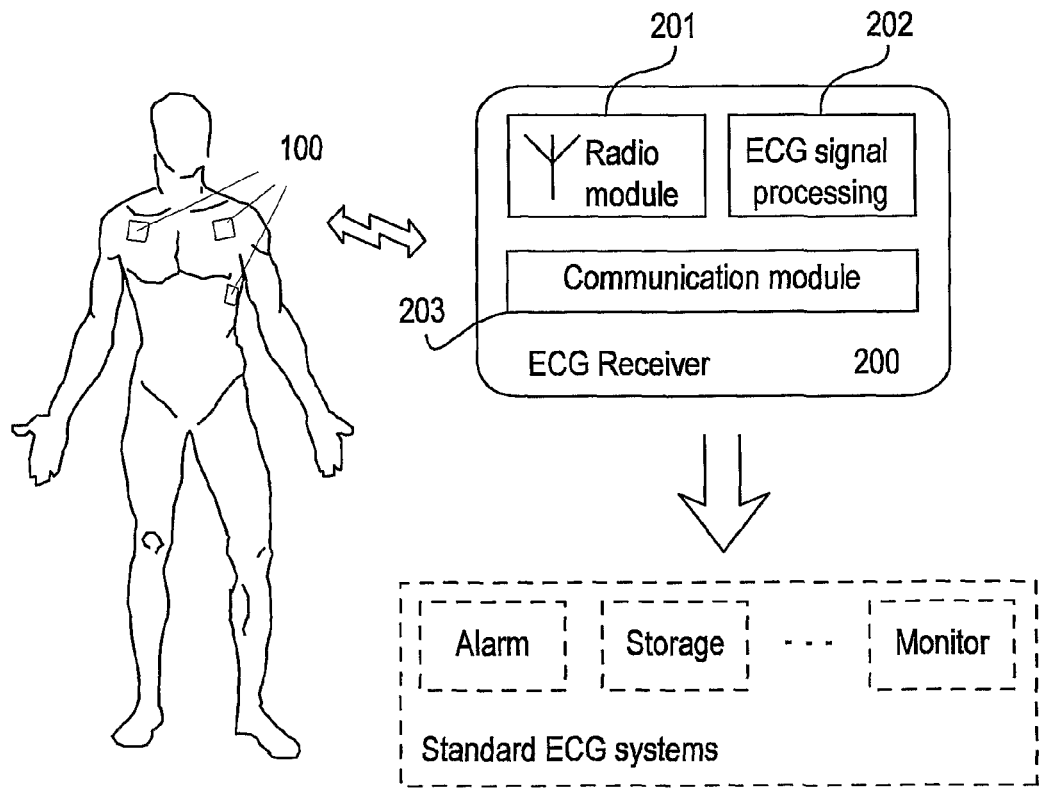
FIG. 4 illustrates an embodiment of a system according to the present invention.

The basic components of the invention are shown in FIG. 4 and consist of at least one mobile ECG sensing unit 100 mounted on the subject and an ECG receiver unit 200, which is a stationary radio unit. The ECG receiver unit 200 comprises a radio module 201 with transmitting and receiving capability, a computation module 202 capable of processing and synthesizing ECG signals, and a communication module 203 for communicating with other standard ECG systems (shown in dashed lines). The mobile units 100, also shown in FIGS. 8 and 10, cooperate during an initial phase of the operation of the system with a connection unit 400. During this initial phase each mobile unit 100 is connected by a multi cable connection 111 to the connection unit 400, which also is connected by single cable connection 401 to each one of a plurality of passive sensing units 403. The cable connections 111, 402 and the connection unit 400 are initially interconnected for the recording of standard ECG signals simultaneously with local bipolar ECG signals. After a shorter recording session, seconds to minutes, the system is calibrated and the connection unit 400 with its cable connections 111 and 401 and the passive electrodes 403 will be removed, as shown in FIG. 4.

Preferably, three ECG sensing units 100 should be used on the same subject for synthesizing the most common type of ECG leads, i.e. 12-lead ECG or equivalent. The ECG sensing units 100 should be placed on strategic locations on the torso, FIG. 4, or as to the chest leads on EASI positions (standard positions known by the man skilled in the art). Any other number of ECG sensing units 100 could be used, i.e. one or more units. The accuracy of the synthesized standard ECG will increase with the number of ECG sensing units used.

Figure 8:
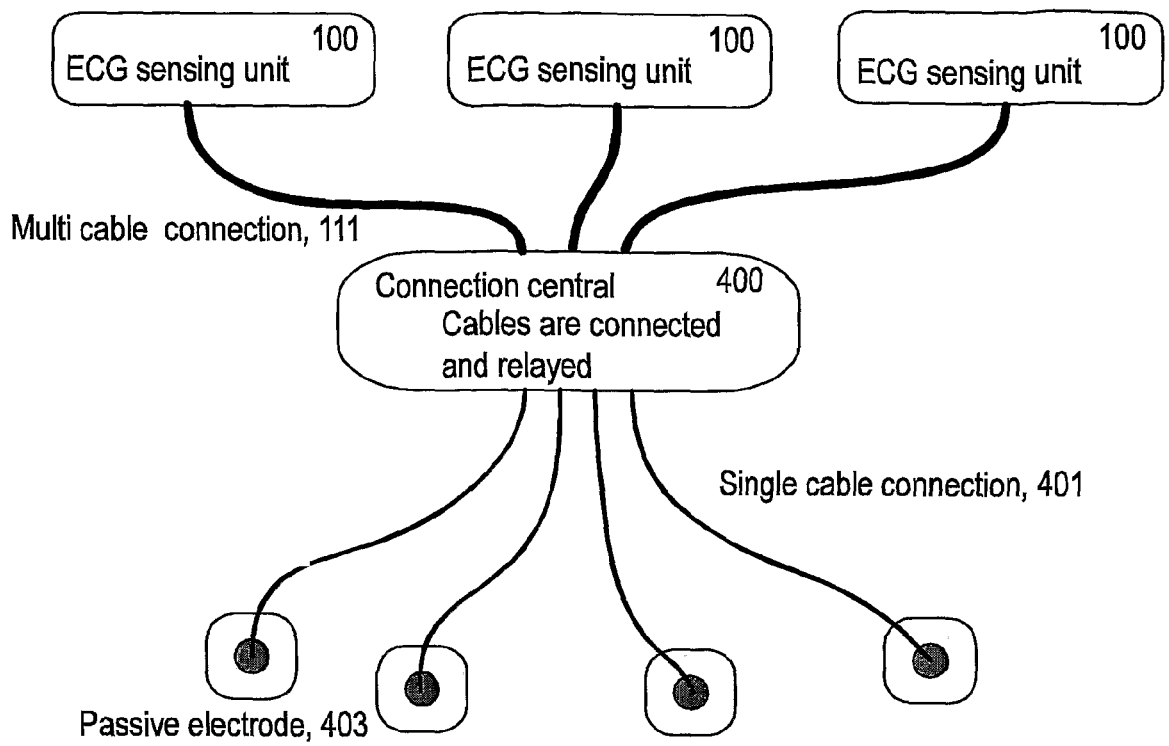
FIG. 8 is a schematic representation of elements of an embodiment of the present invention to be applied to a human subject.
Figure 10:
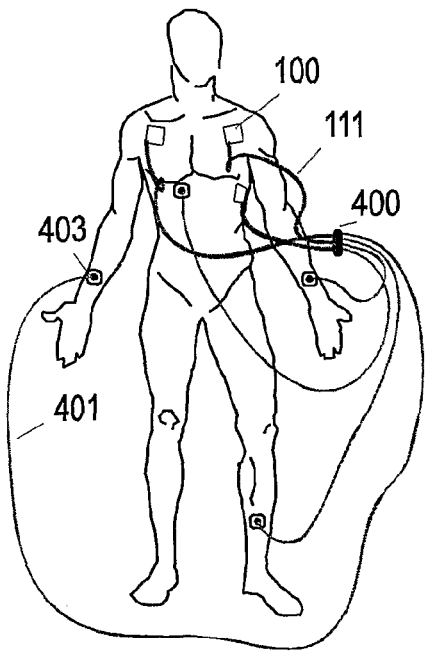
FIG. 10 illustrates the elements of FIG. 8 applied to a human subject.

In a preferred embodiment, three ECG sensing units 100 are initially connected to each other and to four passive electrodes 403. The passive electrodes 403 are applied to the limbs and, optionally, to the chest in order to generate reference ECG signals that are measured in the ECG sensing units 100. A schematic block diagram of the preferred embodiment of these elements is shown in FIG. 8. These elements are intended for calibrating the transform parameters to retrieve correct synthesized standard ECG signals. In FIG. 10 the cables 111 and 401 are connected for calibration and in FIG. 4 the cables have been removed and the ECG leads are synthesized by using the local bipolar ECG measured with the ECG sensing units 100.

Figure 5A:
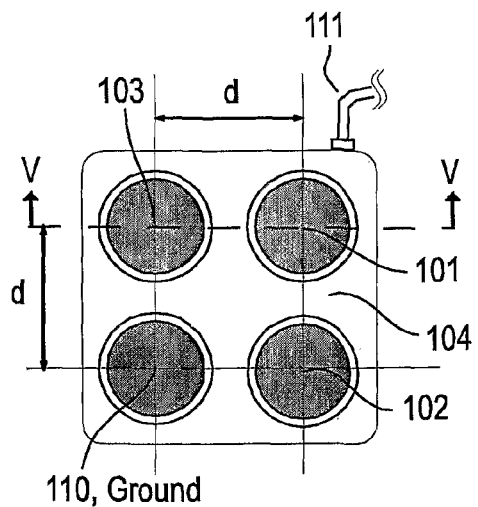
FIG. 5A is a bottom view of a first embodiment of an ECG sensing unit and FIG. 5B is a sectional view along the line V-V.
Figure 5B:
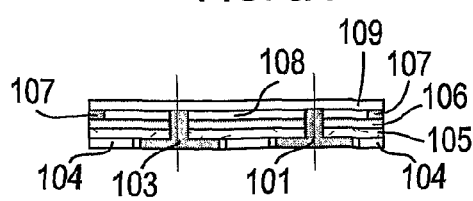

The wireless ECG sensing unit 100 disclosed herein is preferably implemented as an integrated adhesive disposable patch, FIGS. 5A, 5B, for applying to a subject's body and for obtaining and transferring local non-standard ECG data and standard ECG data to the receiver unit 200, shown in FIG. 4. Alternatively, the ECG sensing unit 100 may be implemented as reusable unit with snap connections to available disposable electrodes.

Referring to FIGS. 5A, 5B, the physical embodiment of the ECG sensing unit 100 comprises adhesive means 104 for attaching the device to a subject's body or to a patch on the subject's body, electrodes 101-103 and 110, a structural support means 105 for supporting the electrodes, power supply means 105, an antenna 107, electronic circuits 108, means 109 for isolation and protection, and an input for the multi cable connection 111 connecting the ECG sensing unit 100 to the connection unit 400 and thereby to the passive electrodes 403 and other ECG sensing units 101.

Figure 6A:
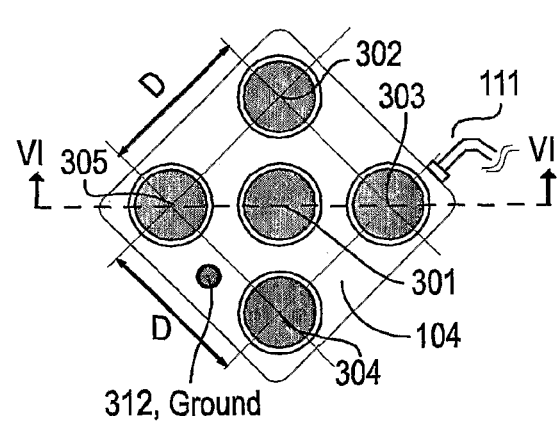
FIG. 6A is a bottom view of a second embodiment of an ECG sensing unit and FIG. 6B is a sectional view along the line VI-VI.
Figure 6B:
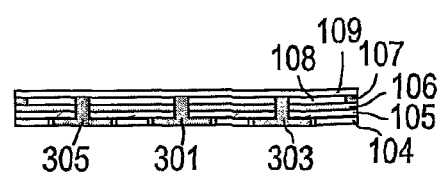
Figure 7A:
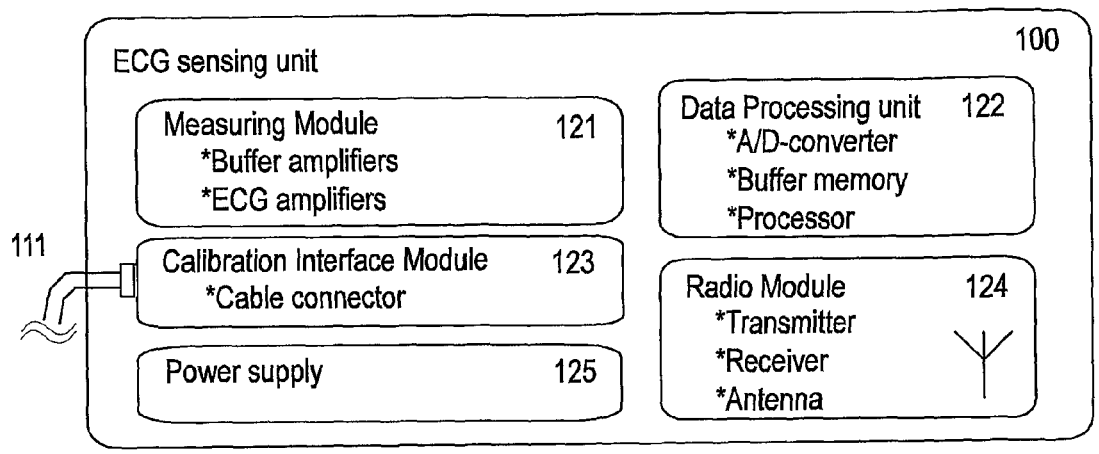
FIG. 7A is a schematic representation of the electronics of an ECG sensing unit.
Figure 7B:
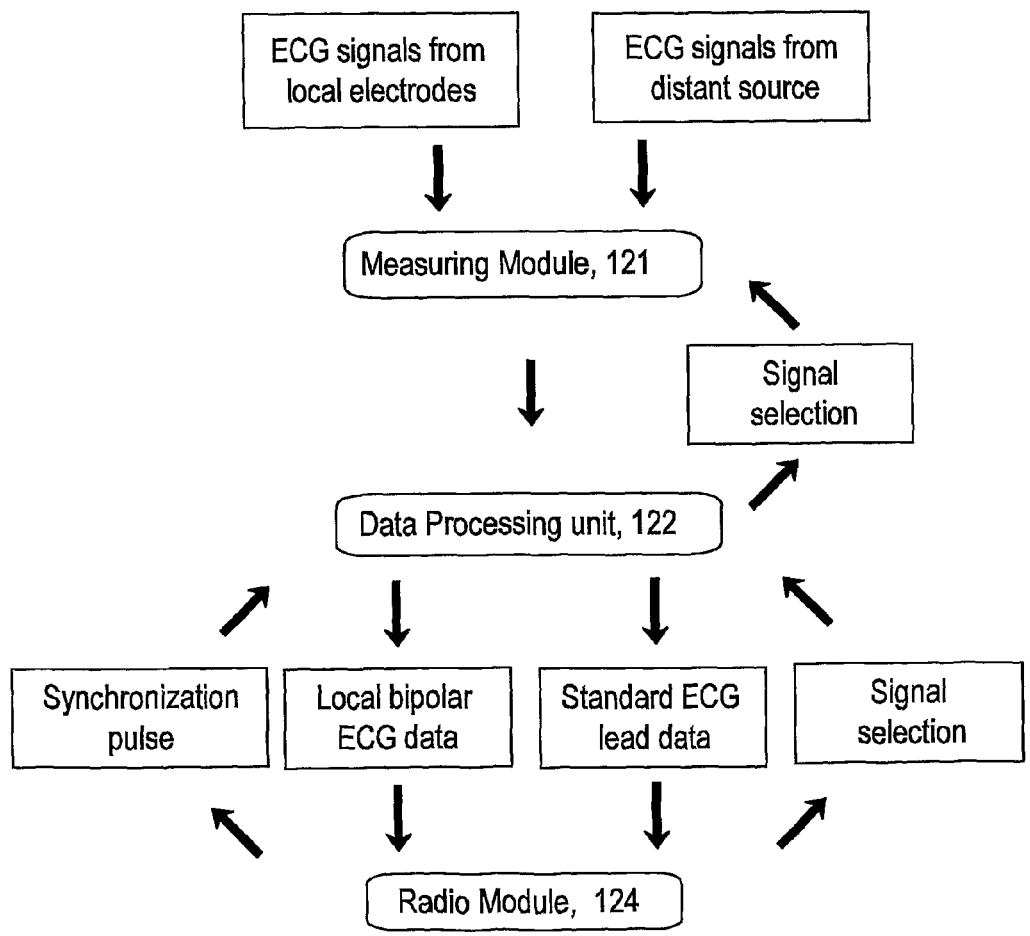
FIG. 7B is a chart illustrating the data flow in the ECG sensing unit.

FIGS. 6A, 6B show an alternative physical embodiment 300 of the ECG sensing unit 100 where the physical coverage is extended using additional measuring electrodes 301, 302, 303, 304, 305 and 312, arranged further apart. In another embodiment the ground electrode 110 and 312, in FIGS. 5A, 5B and FIGS. 6A, 6B respectively, would be excluded as the terminal ground could be connected to patient ground via the measuring electrodes.

The electronic functionality of the preferred embodiment of the ECG sensing unit 100, shown in FIGS. 5A, 5B and 7A, 7B, comprises a measuring module 121, a data processing and storing unit 122, a calibration interface module 123, a radio module 123 for transmitting ECG data to the ECG receiver unit 200 and power supply means 125. ECG signals from the local electrodes 101-103 and calibration ECG signals from the calibration interface module 123, originating from the multi cable connection 111, are subtracted and amplified with common ECG amplifiers, FIG. 2. The local bipolar ECG signals and standard ECG signals are sent to the data processing unit 122, FIG. 7A, 7B, where the data are A/D-converted and stored intermediately before transmission via the radio module 124.

Figure 9:
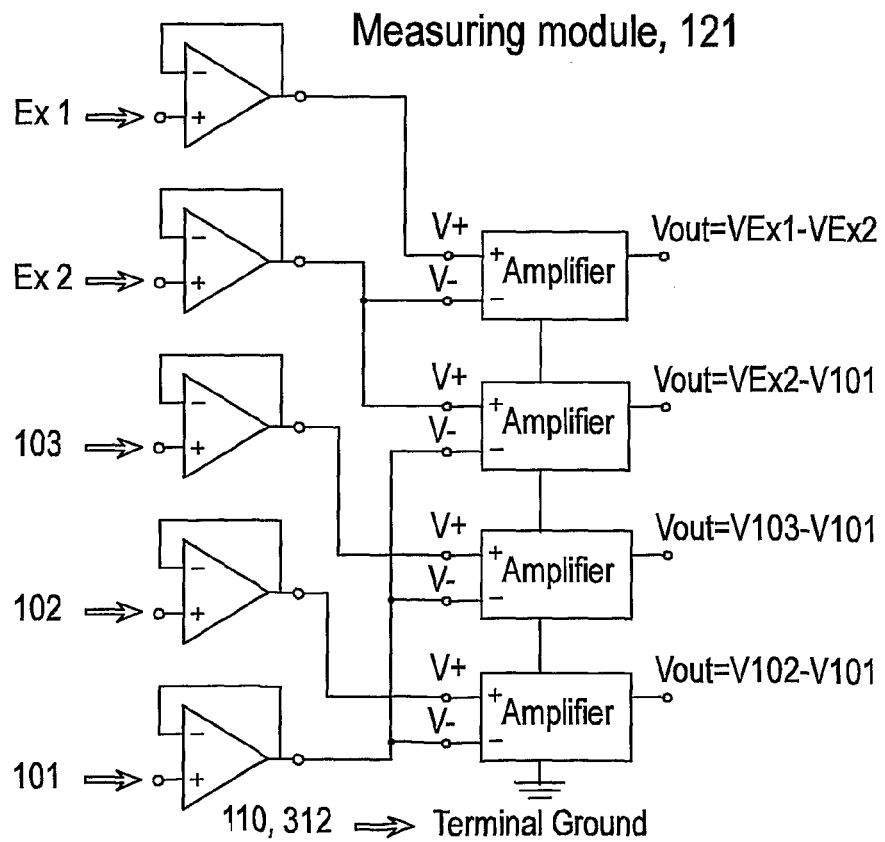
FIG. 9 is a block diagram of a measuring module of the ECG sensing unit.

Referring to FIG. 9, signals $V_{101}$, $V_{102}$ and $V_{103}$ from the three electrodes 101, 102 and 103 are first buffer amplified and are thereafter used to retrieve two local orthogonal bipolar ECG signals $V_{102}-V_{101}$ and $V_{103}-V_{101}$. Two external signals $V_{EX1}$ and $V_{EX2}$ are also first buffer amplified and thereafter used to retrieve the difference signals $V_{EX1}-V_{EX2}$ and $V_{EX2}-V_{101}$. The two external signals $V_{EX1}$ and $V_{EX2}$ originating from the multi cable connection 111 in FIG. 5 are used only during the calibration procedure.

The preferred measuring embodiment is shown in FIGS. 5A, 5B where an ECG is measured locally from each ECG sensing unit 100. The measuring electrodes 101-103 are arranged orthogonally, i.e. the voltage potentials that are measured are $V_{102}-V_{101}$ and $V_{103}-V_{101}$. These two measurements are later referred to as a 2-dimensional ECG; the angle could however be less than 90° but should be substantially larger than 0°. The local measurements are more generally referred to as local bipolar ECGs. Subject's ground potential is connected via the electrode 110 and is then connected to the ECG sensing units terminal ground. In an alternative solution, this is accomplished by driving the ECG sensing unit's terminal ground to patient ground through the measuring electrodes 101, 102 and 103 by a technique well known to a man skilled in the art. The ground electrode in FIGS. 5A, 5B and 6A, 6B would in these embodiments be excluded. The preferred distance d in FIG. 5A between the electrode 101 and the electrode 102 and 103, respectively, is 2-7 cm, i.e. the distance from center to center of those electrode. The parameter d and the placement of the ECG sensing units 100 will be discussed in the following paragraph.

Figure 11A:
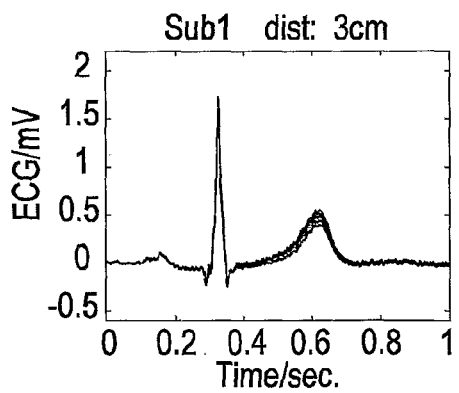
FIGS. 11 A-D are recordings performed on two human subjects with closely located electrodes.
Figure 11B:
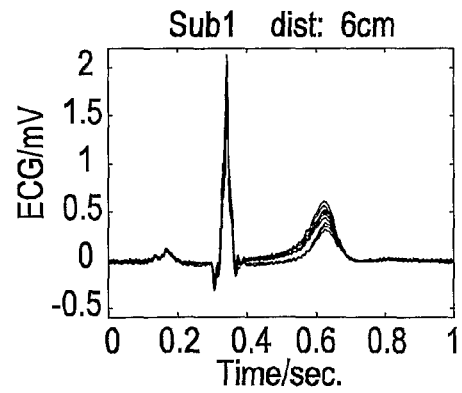
Figure 11C:
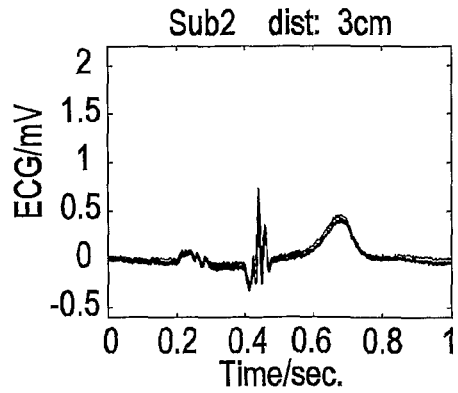
Figure 11D:
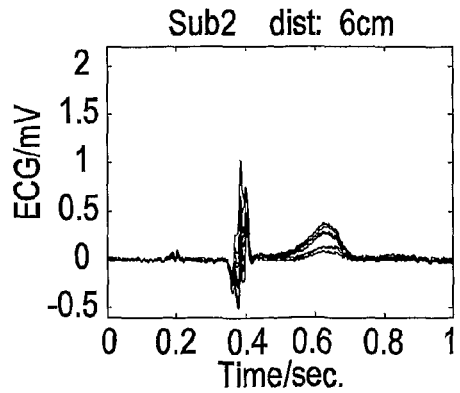

The ECG potentials on the body may be seen as a stationary current dipole. The bio-potential field has larger divergence closer to the heart. Therefore local bipolar ECG measurements will be larger closer to the heart. The ECG sensing unit 100 should therefore preferably be placed on the torso on different sides of the heart, e.g. in the same positions as the EASI system (position E, A, S and I) or as shown in FIG. 4. The distance d in FIG. 5A is an important parameter. As d increases the bipolar ECG signal amplitude will too. In FIGS. 11A-D ECG was recorded with one reference voltage on the left leg and nine electrodes arranged in a formation of a 3×3 array. The recordings were performed on two adult subjects (FIGS. 11A, 11B and 11C, 11D respectively) with two different orthogonal distances between the electrodes, i.e. 1.5 cm (FIGS. 11A, 11C) and 3 cm (FIGS. 11B and 11D). The scaling in FIGS. 11A-D is the same. It is obvious that the ECG curves have a larger variation for electrodes located further away, i.e. in the diagrams of FIGS. 11B and 11D.

Figure 12A:
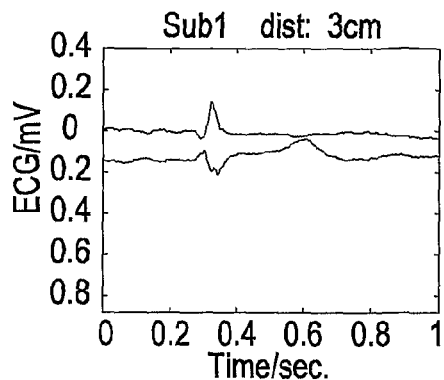
FIGS. 12 A-D are recordings of local bipolar signals performed on two human subjects with closely located electrodes.
Figure 12B:
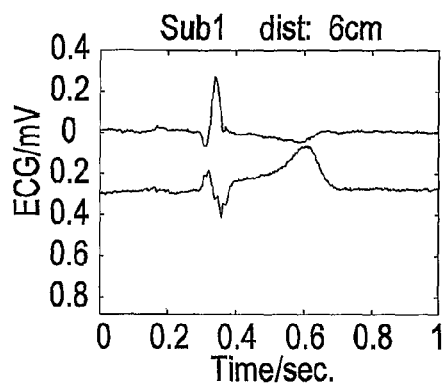
Figure 12C:
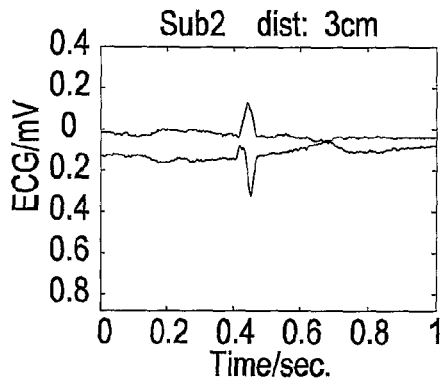
Figure 12D:
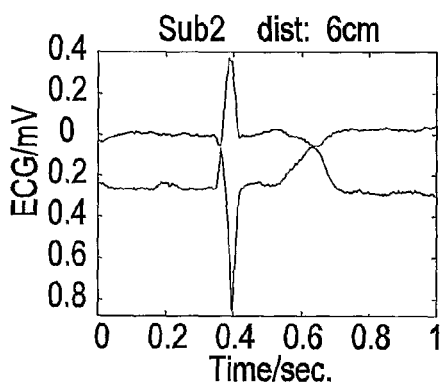
Figure 13A:
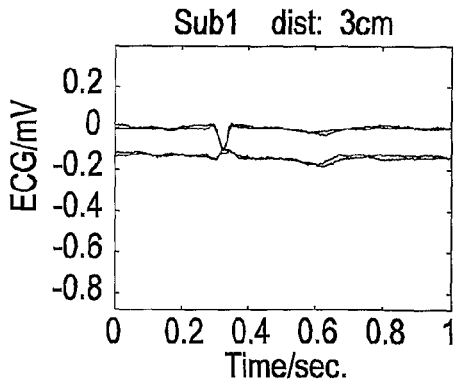
FIGS. 13 A-D are multiple recordings of local bipolar signals performed on two human subjects with closely located electrodes.
Figure 13B:
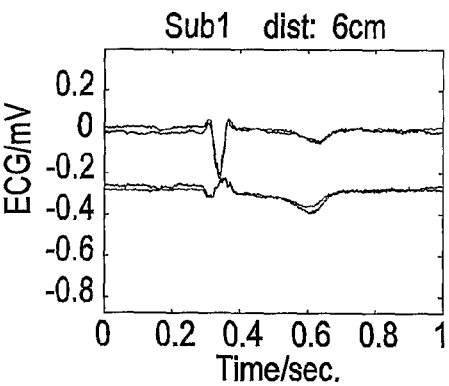
Figure 13C:
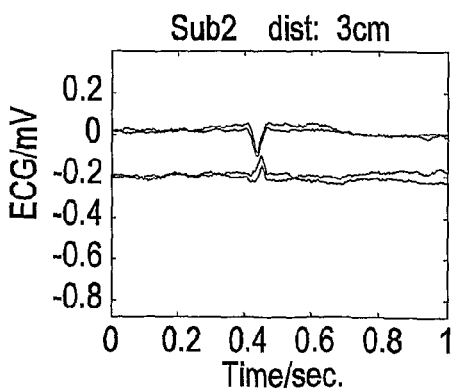
Figure 13D:
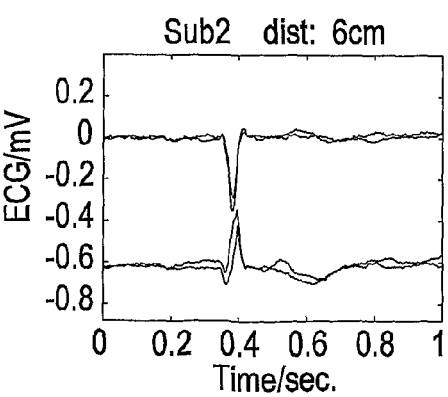
Figure 14:
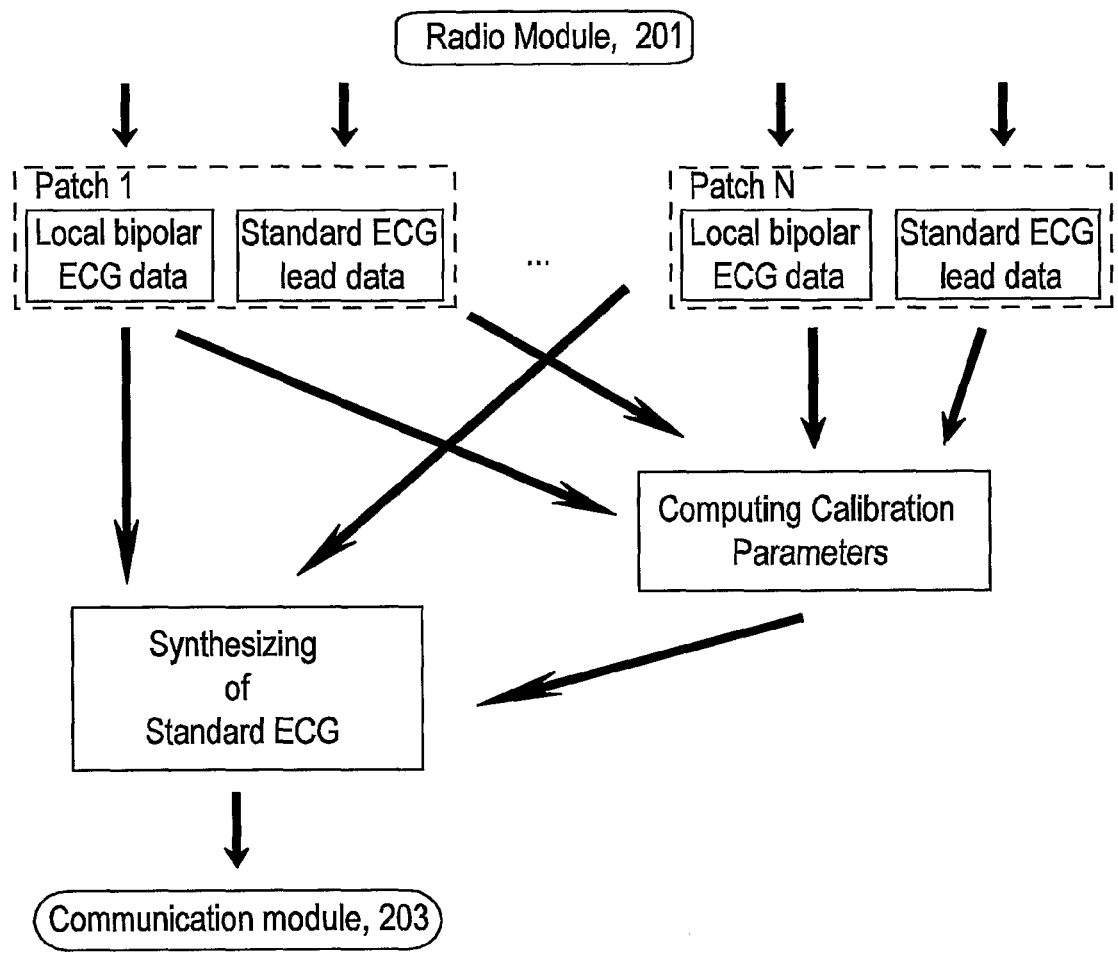
FIG. 14 is a chart illustrating the flow of ECG data through the ECG receiver unit in FIG. 4.
Figure 15:
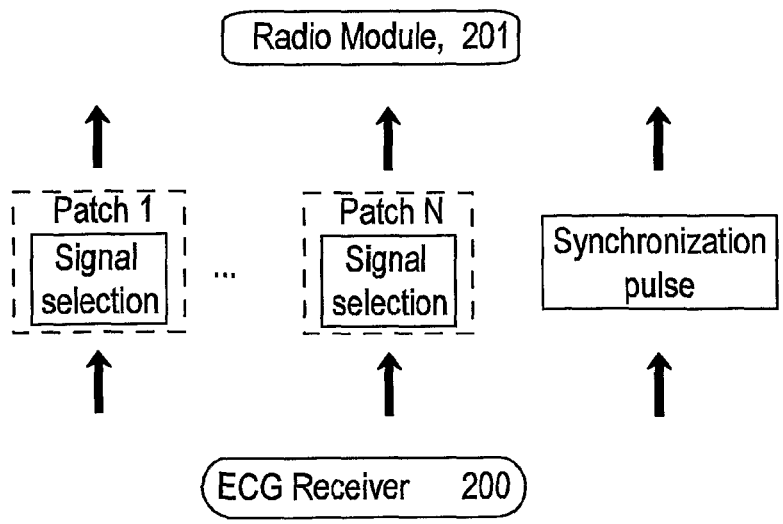
FIG. 15 is a chart illustrating the flow of control signals through the ECG receiver unit in FIG. 4.

In FIGS. 12A-D, the local bipolar ECGs are displayed computed from the recordings in FIGS. 11A-D. The heart beat in FIGS. 11A-D and FIGS. 12A-D is thus one and the same. The topmost curve in each diagram of FIGS. 12A-D is detected in a horizontal or X-axis direction while the lower curve is detected in a vertical or Y-axis direction, i.e. orthogonal to the X-axis. These curves are typical curves recorded with the ECG sensing unit 100 placed on the left chest under the collar bone. FIGS. 12A-D show that recordings performed with the electrodes placed further apart result in higher registered ECG signals (FIGS. 12B and 12D). The distance between the local electrodes used in FIGS. 12A and 12B was 3 cm and the distance between the local electrodes used in FIGS. 12C and 12D was 6 cm.

In FIGS. 13A-D a comparison between two closely located 2-dimensional local ECG recordings was simulated utilizing the recordings in FIGS. 11A-D. The distances between the ECG sensing units were thus 1.5 cm for FIGS. 13A and 13C and 3.0 cm for FIGS. 13B and 13D (both in X and Y direction). There is a close resemblance between the two ECG sensing units in FIGS. 13A-D, as expected since the distance between the units were just 1.5 cm and 3.0 cm. Some of the conclusions from the recordings in FIGS. 11A-D-FIGS. 13A-D are:

1. Two local orthogonal ECG recordings can often be transformed into any other orientation on the skin surface with high precision. Therefore the synthesis of standard ECG will have little gain of more local recordings than the orthogonal X and Y directions as long as the distance between the electrodes is small.
2. Increasing the distance between the electrodes will increase local ECG amplitude and thus generate more robust synthesized standard ECG signals.

3. The ECG sensing units should preferably be evenly spread around the heart/chest for gathering of uncorrelated data and thus generating better synthesized ECG signals.
4. The local ECG sensing units should preferably be placed on the torso due to the fact that the ECG signals are measured differentially locally and thus the signal strengths would be very low on the limbs.
5. The standard ECG signals can not be retrieved by some simple scaling of the local ECG signals. Instead the bipolar local ECG signals must be mathematically transformed into standard ECG leads (synthesized).

If the distance d is too small the bipolar ECG signals will be buried in the noise. If d is increased the signals will increase and in the most extreme variant the measuring electrodes will be positioned as in the EASI system, stretching over the whole torso. However, in the EASI system four unipolar measurements are used to synthesize a standard 12-lead system. According to the present invention, the use of local bipolar measurements is disclosed for synthesizing standard ECG leads. The practical advantage of local measurements, compared to the EASI system and other similar systems, are obvious as no wires are required on the body, as shown in FIG. 4. In the procedure of synthesizing ECG from non-standard electrode placement (such as the EASI system and the system disclosed herein) parameters are used to transform the non uniform ECG to standard ECG leads. However, the variance in body impedance between different people is an evident source of error. According to the present invention, this problem is overcome by using an initial calibration procedure wherein standard ECG leads are recorded synchronous with the local bipolar ECG signals.

The following methods are examples of different solutions. However, the invention is not limited to these examples.

Some standard ECG leads are described above and some of the standard leads are computed by combining signals originating from several different locations of the body. This computation has in older ECG recording units normally been done by analogue circuits. However, all the standard ECG lead can be calculated afterwards as long as all anatomical positions are covered. For example a doctor wants to measure at least lead II, V1 and V6 with the invention. Two ECG sensing units 100 are then placed on the body, one on V1 and one on V6. The passive electrodes 403, connected to the ECG sensing unit 100, are then placed on left arm, right arm and left leg (LA, RA and LL). The system records the ECG signals and when calibrated the passive electrodes 403 together with the cables 111 and 402 are removed. The system will then with high accuracy synthesize all standard leads that are normally retrieved from the just mentioned anatomical position, i.e. lead I, II, III, aVR, aVL, aVF, V1 and V6. From these leads it is possible to further synthesize other leads, but with less accuracy. Preferably, additional ECG sensing units 100 should be applied on the additional desired ECG lead.

In the example above the ECG sensing unit 100 placed at V1 will record V1-LF with the help of external signals. The V1 lead should be referenced to the Wilson central terminal (CT) which is a linear combination of the LA, RA and LL. Thus it is possible to calculate the correct lead V1 (with the CT as reference) simply by a linear combination of lead I, II, III and the recording (V1-LL). This is easily understood by a person with basic knowledge in linear algebra, i.e. a person skilled in the art.

The initial calibration phase will be described more in detail referring to FIGS. 7B and 14-18.

The calibration is started from the ECG receiver unit 200 which sends selection signals and synchronization pulses via its radio module 201 to the radio module 124 of each ECG sensing unit 100. As a consequence, preselected passive electrodes 403 are connected to each ECG sensing unit in predetermined sequences such that the measuring module 121 of each ECG sensing unit 100 generates signals of the type illustrated in FIG. 9. Following an A/D-conversion and a data processing in the data processing unit 122, local bipolar data for each ECG sensing unit 100 and calculated standard ECG data are stored digitally in a buffer memory in the data processing unit 122. These digitally stored data representing one and the same heart beat, are then compared in order to determine the parameters of a transfer function by which the standard ECG leads may be synthesized from the local bipolar ECG data.

Once these parameters have been determined, the calibration phase is terminated and the passive electrodes 403 may be detached from the body of the patient and the multi cable connection 111 be disconnected from the ECG sensing units 100.

During the following operation of the system, the local bipolar data resulting from the bipolar signals detected by the ECG sensing units 100 are used for synthesizing the standard ECG leads, the ECG sensing units 100 and the ECG receiver unit 200 communicating wireless during this operation. Thus, wires are used only during the initial calibration phase.

Figure 17:
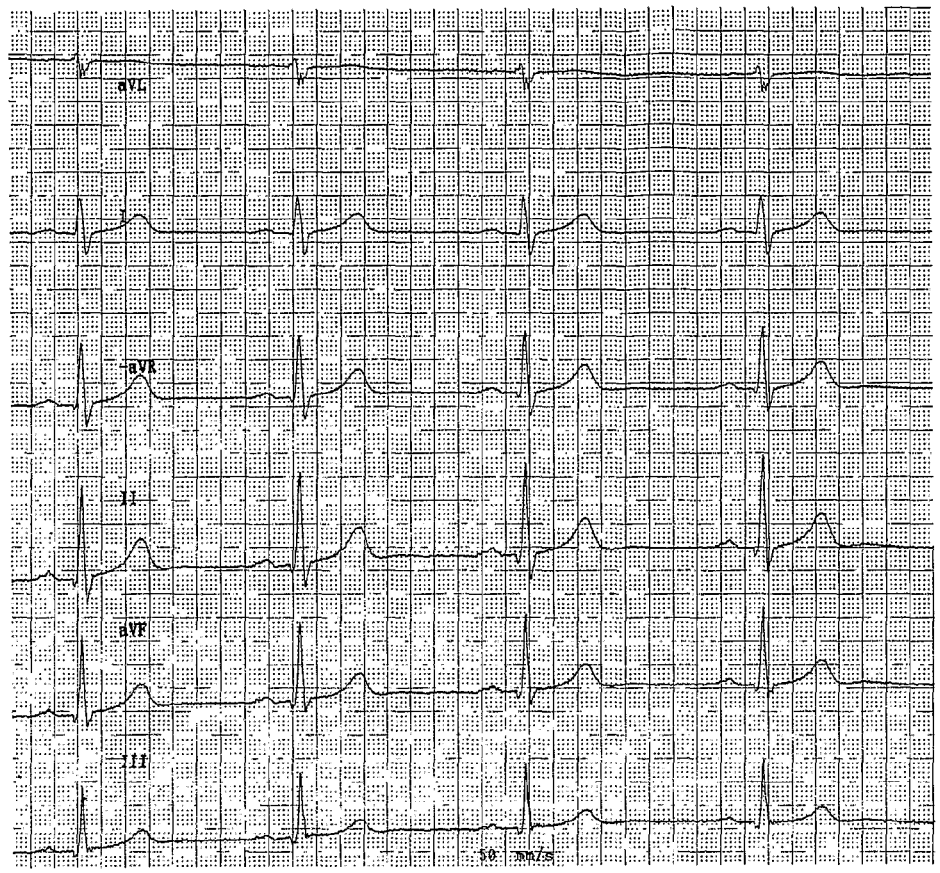
FIG. 17 shows ECG leads recorded with standard equipment.
Figure 18:
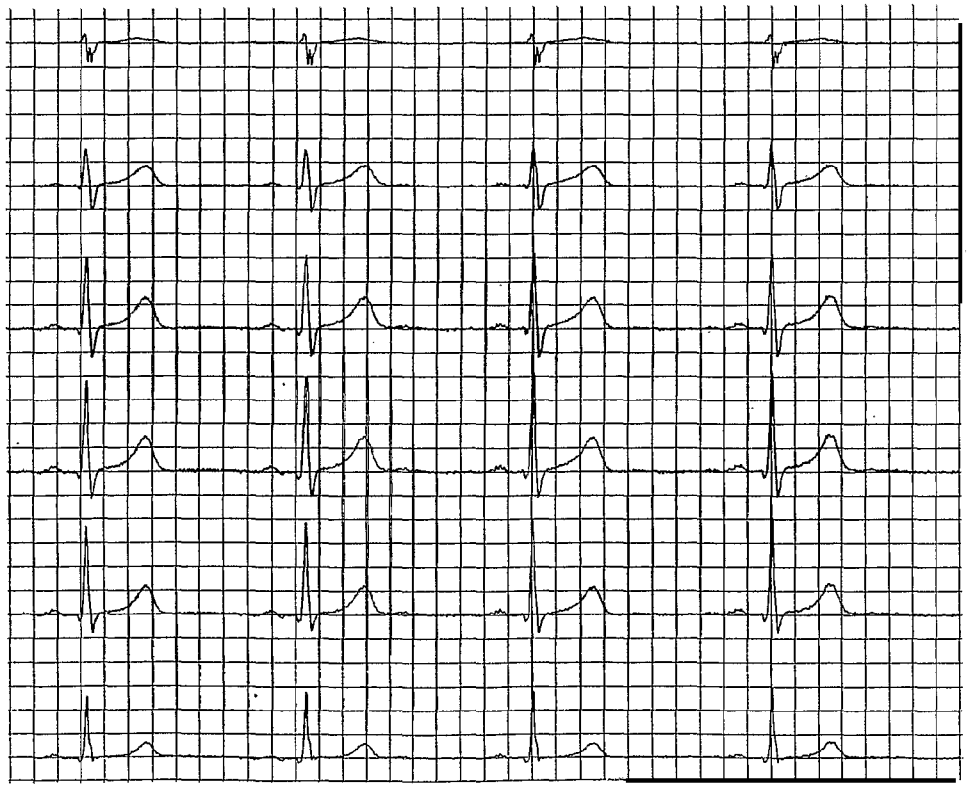
FIG. 18 shows simultaneously recorded ECG signals recorded with the equipment according the present invention.

The effect of the system according to the present invention is illustrated in FIGS. 17 and 18, FIG. 17 showing six standard ECG leads obtained by a commercially available ECG equipment and FIG. 18 showing synthesized ECG leads solely based on the bipolar ECG signals obtained according to the present invention simultaneously therewith.

The synthesizing of standard ECG leads according to the present invention is performed with two major differences relative most common methods for synthesizing of standard ECG leads. A first difference is that the standard ECG leads are recorded in an initial calibration procedure where these standard ECG leads are used to retrieve optimal individual adaptation of the transformation parameters. Secondly, the multiple electrodes are organized in groups better suited for totally wireless solutions, each group recording bipolar ECG signals locally.

In the preferred embodiment, three ECG sensing units 100 are placed around the heart and give a total of six ECG signals and 6-10 standard ECG leads (in the calibration phase) depending on placement of the ECG sensing units 100 and the passive electrodes 403. The six bipolar ECG signals are then transformed so that the different synthesized ECG leads do not deviate from the recorded standard ECG leads. Mathematically, this could be seen as the six bipolar ECG signals are input signals to a transfer function and the standard ECG leads are output signals from the same transfer function. As both the input signals and the output signals are known (in the calibration phase), the transfer function parameters can be computed. However, a properly suited transfer function has to be selected. In the simplest case a matrix is multiplied with the input signals to calculate the output signals. However, using three ECG sensing units 100 will not always be sufficient for obtaining adequately synthesized ECG leads. Therefore phase information is computed for different combinations of local bipolar ECG signals. The input space was extended to 18 input signals thus adding 12 signals containing phase information. The algorithm to retrieve the phase information can be seen in the following formula (1)-(12). The variable labeled ut is the 12 added channels with phase information while the variable d is the initially recorded bipolar ECG signals. Note that all variables are vectors, e.g. d[0] is the recorded vector for bipolar channel 0.

$$ut[6]=(d[0]*d[2]-d[1]*d[3])/sqrt(d[2]*d[2]+d[3]*d[3]+0.1); \quad (1)$$

$$ut[7]=(d[0]*d[3]+d[1]*d[2])/sqrt(d[2]*d[2]+d[3]*d[3]+0.1); \quad (2)$$

$$ut[8]=(d[0]*d[2]-d[1]*d[3])/sqrt(d[0]*d[0]+d[1]*d[1]+0.1); \quad (3)$$

$$ut[9]=(d[0]*d[3]+d[1]*d[2])/sqrt(d[0]*d[0]+d[1]*d[1]+0.1); \quad (4)$$

$$ut[10]=(d[0]*d[4]-d[1]*d[5])/sqrt(d[4]*d[4]+d[5]*d[5]+0.1); \quad (5)$$

$$ut[11]=(d[0]*d[5]+d[1]*d[4])/sqrt(d[4]*d[4]+d[5]*d[5]+0.1); \quad (6)$$

$$ut[12]=(d[0]*d[4]-d[1]*d[5])/sqrt(d[0]*d[0]+d[1]*d[1]+0.1); \quad (7)$$

$$ut[13]=(d[0]*d[5]+d[1]*d[4])/sqrt(d[0]*d[0]+d[1]*d[1]+0.1); \quad (8)$$

$$ut[14]=(d[2]*d[4]-d[3]*d[5])/sqrt(d[4]*d[4]+d[5]*d[5]+0.1); \quad (9)$$

$$ut[15]=(d[2]*d[5]+d[3]*d[4])/sqrt(d[4]*d[4]+d[5]*d[5]+0.1); \quad (10)$$

$$ut[16]=(d[2]*d[4]-d[3]*d[5])/sqrt(d[2]*d[2]+d[3]*d[3]+0.1); \quad (11)$$

$$ut[17]=(d[2]*d[5]+d[3]*d[4])/sqrt(d[2]*d[2]+d[3]*d[3]+0.1); \quad (12)$$

Figure 16:
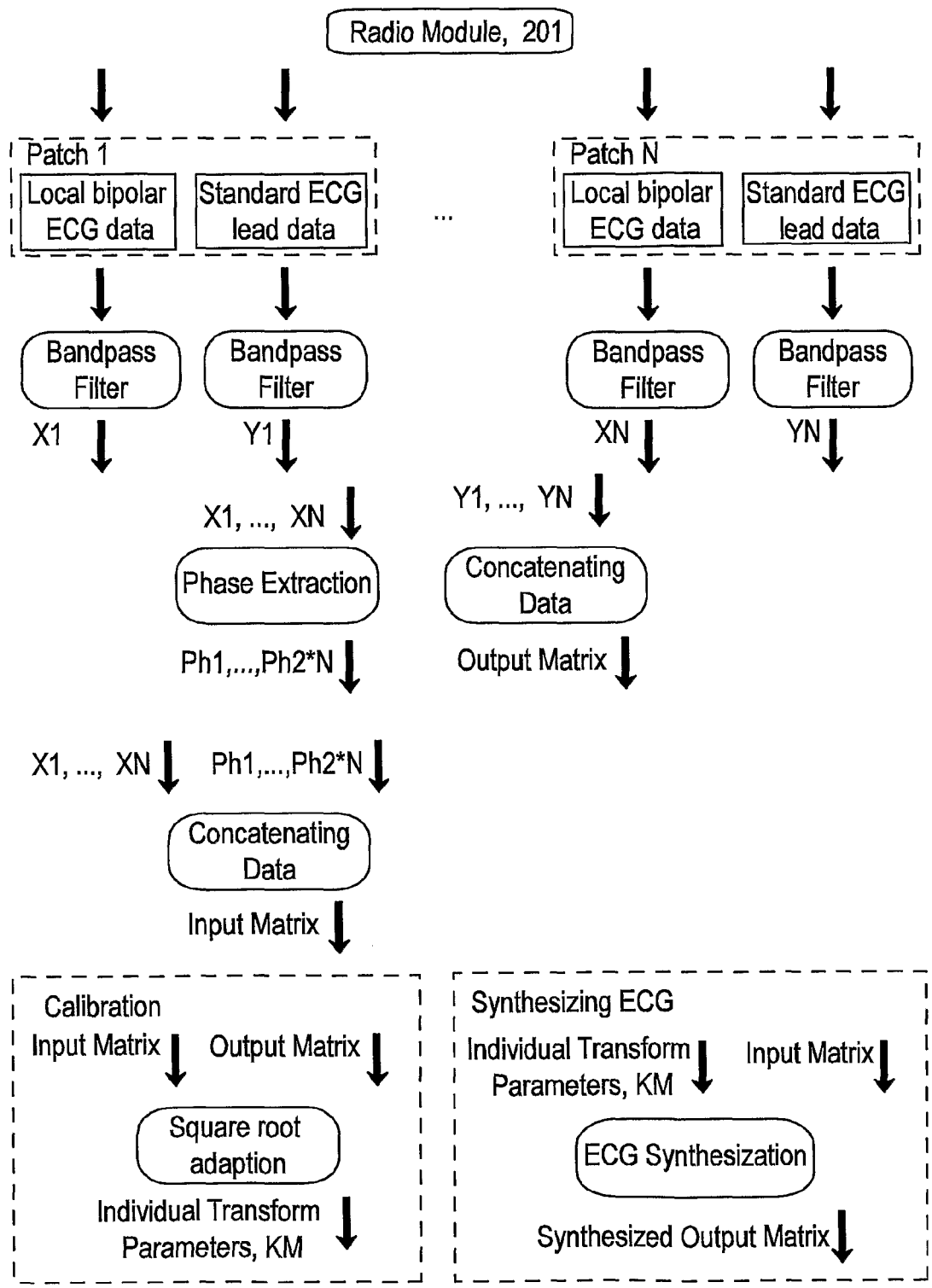
FIG. 16 is a chart illustrating the synthesizing and calibration of ECG signals.

FIG. 16 shows the data flow of the synthesizing in the ECG receiver. ECG information comes from the radio modul 201 from each ECG sensing unit. In FIG. 16 the information from one patient with N ECG sensing units 100 is shown. Each ECG sensing unit 100 transmits bipolar ECG data and initially also standard ECG data. The ECG data is first digitally band pass filtered to remove influence from moving base line and high frequency noise. The bipolar ECG signals are called X and the standard ECG signals are called Y and are indexed with a number representing the channel. Thereafter the phase information, denoted Ph, is retrieved using the bipolar ECG signals X. The retrieval of the phase information is described above and in formula (1)-(12). The bipolar ECG signals X together with the phase information Ph are then grouped into an "input matrix", while the "output matrix" is formed with the ECG standard leads Y. The least square method is used to retrieve the individual transform parameters KM for the transfer function. These KM parameters are only retrieved in the calibration phase of the system when the standard leads are present. When the cables have been removed, the ECG is synthesized by multiplying the Input matrix with the transfer parameters KM. The individual transform parameters KM is in this example 18 elements long for each standard lead synthesized.

The present invention is described with reference to specific embodiments related to ECG. However, other embodiments than those preferred are equally possible within the scope of the appended claims, e.g. different arrangement of electrodes or electronic circuits than those described, performing the invention method by hardware or software, etc. Applications and use of the above described measurement system and method according to the invention are various.

As an example, it should be noted that one or more electrodes of one ECG sensing unit could be used as a passive electrode for another ECG sensing unit.

Furthermore, the term "comprises/comprising" when used in this specification does not exclude other elements or steps, the terms "a" and "an" do not exclude a plurality and a single processor or other units may fulfill the functions of several of the units or circuits recited in the claims.

The invention claimed is:

1. system for wireless generation of at least one standard ECG lead, comprising
   a plurality of electrodes for application to a subject at separate points thereof, said plurality of electrodes being grouped into a first group and a second group;
   connections allowing physical and electrical connection and disconnection of electrodes of said first group of electrodes with each other and from each other;
   a remote receiver station;
   a generator for generating a standard ECG lead from signals detected by said first group of said plurality of electrodes;
   a plurality of wireless ECG sensing units each comprising:
      a radio module for communication with said remote receiver station, and
      at least three non-linearly arranged and closely located electrodes belonging to said second group of said plurality of electrodes, wherein said at least three non-linearly arranged and closely located electrodes are arranged for detecting two local bipolar signals,
   wherein each of said wireless ECG sensing units is arranged to generate at least two non-standard ECG signals from said bipolar signals, and
   wherein said radio module of each of said wireless ECG sensing units is arranged for wireless transferring of said non-standard ECG signals to said remote receiver station,
   wherein the system further comprises a computation module in said remote receiver station for calculation of a transform synthesizing said generated standard ECG lead from at least two of said non-standard ECG signals,
   wherein said computation module is further arranged to synthesize said standard ECG lead from said non-standard ECG signals solely using said transform following a disconnection of electrodes of said first group of electrodes from each other,
   whereby said at least one standard ECG lead is wireless generated by said synthesizing following the disconnection of electrodes of said first group of electrodes from each other.

2. A system for wireless generation of at least one standard ECG lead according to claim 1, wherein the electrodes of each of said plurality of wireless ECG sensing units are arranged along two orthogonal lines.

3. A system for wireless generation of at least one standard ECG lead according to claim 1, wherein said radio module of each wireless ECG sensing unit is arranged to be activated by said remote receiver station.

4. A system for wireless generation of at least one standard ECG lead according to claim 1, wherein each of said wireless ECG sensing unit further comprises a differential amplifier for each bipolar signal and a data processor connected between said differential amplifiers and said radio module and adapted for digital storing of the non-standard ECG signals.

5. A system for wireless generation of at least one standard ECG lead according to claim 4, wherein each of said wireless ECG sensing units further comprises at least one further differential amplifier having inputs connectable to separate ones of said plurality of electrodes and an output connected to said data processor.

6. A system for wireless generation of at least one standard ECG lead according to claim 5, wherein said connections allowing physical and electrical connection and disconnection of said electrodes of said first group of electrodes comprises wires connected to the electrodes in said first group of said plurality of electrodes and a switch for selecting the electrodes to be connected to said at least one further differential amplifier.

7. A system for wireless generation of at least one standard ECG lead according to claim 6, wherein said connections allowing physical and electrical connection and disconnection of said electrodes of said first group of electrodes also comprises wires each connected to one electrode in a separate wireless ECG sensing unit.

8. A system for wireless generation of at least one standard ECG lead according to claim 6, wherein each wireless ECG sensing unit comprises a controller for controlling the switch.

9. A system for wireless generation of at least one standard ECG lead according to claim 1, comprising a synchronizing unit in said remote receiver station for synchronizing data flow from the wireless ECG sensing units.

10. A system for wireless generation of at least one standard ECG lead according to claim 1, wherein each of said plurality of wireless ECG sensing units further comprises a cable connection allowing physical and electrical connection and disconnection of said wireless ECG sensing unit with another wireless ECG sensing unit.

11. A system for wireless generation of at least one standard ECG lead according to claim 1, wherein at least one of said at least three non-linearly arranged and closely located electrodes of at least two of said plurality of wireless ECG sensing unit belongs to said first group of electrodes.

12. A system for wireless generation of at least one standard ECG lead according to claim 1, wherein said generator for generating a standard ECG lead from signals detected by said first group of said plurality of electrodes is located in said remote receiver station.

13. A system for wireless generation of at least one standard ECG lead according to claim 1, wherein at least one of said plurality of wireless ECG sensing units comprises said generator for generating a standard ECG lead from signals detected by said first group of said plurality of electrodes.

* * * * *